US00PP21376P2

(12) United States Plant Patent
Lyrene

(10) Patent No.: US PP21,376 P2
(45) Date of Patent: Oct. 12, 2010

(54) SOUTHERN HIGHBUSH BLUEBERRY PLANT NAMED 'FL04-235'

(50) Latin Name: *Vaccinium corymbosum L.*
Varietal Denomination: FL04-235

(75) Inventor: Paul M. Lyrene, Micanopy, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/584,556

(22) Filed: Sep. 8, 2009

(51) Int. Cl.
*A01H 5/00* (2006.01)

(52) U.S. Cl. ..... Plt./157

(58) Field of Classification Search ..... Plt./157
See application file for complete search history.

*Primary Examiner*—Susan B McCormick Ewoldt
(74) *Attorney, Agent, or Firm*—Jondle & Associates, P.C.

(57) ABSTRACT

'FL04-235' is a new southern highbush blueberry plant distinguished by a low chilling requirement with prolific early-spring leafing, a vigorous and very upright to spreading growth habit, very stout canes, early ripening (50% ripe berries in north Florida by April 15) and berries that are sweet and firm with a small, dry picking scar, is disclosed.

3 Drawing Sheets

Figure 1:
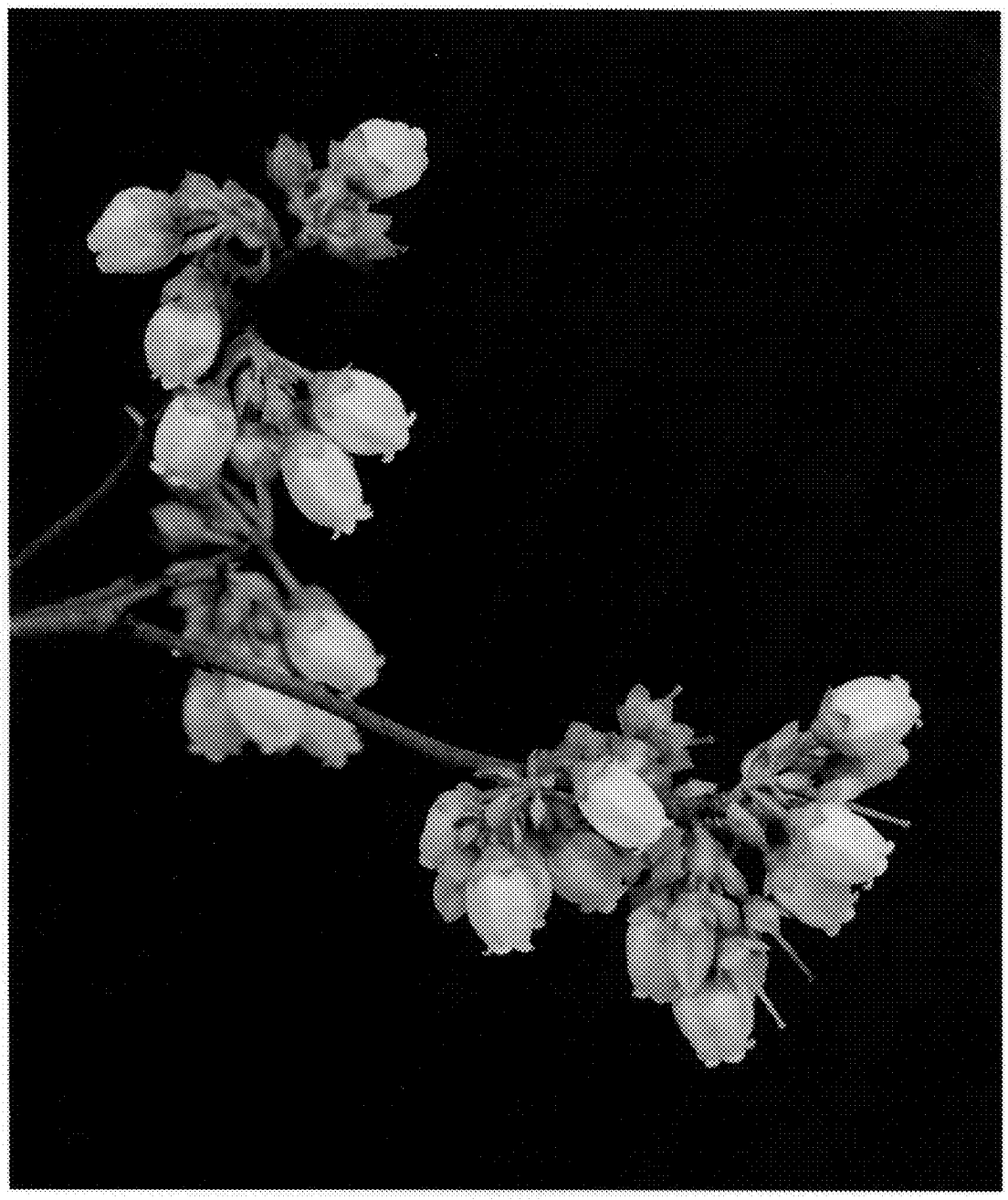

Statement regarding federally sponsored research: The present invention was supported in part by funds from the U.S. Government. The U.S. Government therefore may have certain rights in the invention.

Genus and species: *Vaccinium corymbosum* L.

Variety denomination: 'FL04-235'.

BACKGROUND OF THE INVENTION

The invention relates to a new and distinct variety of a southern highbush blueberry (*Vaccinium corymbosum* L.) hybrid named 'FL04-235'. 'FL04-235' is intended for production of fresh-market blueberries in early spring from areas with mild winters and early spring warmth. 'FL04-235' is a southern highbush blueberry clone distinguished by its low chilling requirement, its vigorous, very upright habit, disease-resistant bush, and by its firm, sweet berries that ripen from early to late-April through early May when grown in north Florida. Several hundred plants of 'FL04-235' have been propagated by softwood cuttings at Gainesville, Fla., and have fruited for several years and the resulting plants have all been phenotypically indistinguishable from the original plant.

'FL04-235' originated as a seedling from the cross of the proprietary *Vaccinium corymbosum* L. female parent, 'FL98-409' (unpatented) with the proprietary *Vaccinium corymbosum* L. male parent, 'C97-390' (unpatented) in a greenhouse in Gainesville, Fla. in February of 2001. The seedling was first fruited in a high-density field nursery in the spring of 2003. After the second year of fruiting in the field in the spring of 2004, the seedling was named 'FL04-235' and was propagated by softwood cuttings. An experimental 15-plant clonal plot was established in Windsor, Fla. in January of 2005. Based on the growth and berry characteristics of this plot, 'FL04-235' was re-propagated by softwood cuttings, and an experimental 200-plant test plot was established in Waldo, Fla. in January of 2008.

'FL04-235' has been reproduced asexually for over six years using softwood cuttings and has been found to retain its distinctive characteristics through successive asexual propagations.

Plant Breeder's Rights for this cultivar have not been applied for. 'FL04-235' has not been made publicly available more than one year prior to the filing date of this application.

SUMMARY OF THE INVENTION

The following are the most outstanding and distinguishing characteristics of 'FL04-235' when grown under normal horticultural practices in north Florida.

1. A very low chilling requirement with prolific early-spring leafing;
2. A vigorous and very upright to spreading growth habit;
3. Very stout canes;
4. Early ripening (50% ripe berries in north Florida by April 15); and
5. Berries that are sweet and firm with a small, dry picking scar.

DESCRIPTION OF THE PHOTOGRAPHS

This new southern highbush blueberry plant is illustrated by the accompanying photographs which show the plant's form, foliage, flower clusters and berry clusters. The colors shown are as true as can be reasonably obtained by conventional photographic procedures.

In the photograph o the flowers in FIG. 1, the flowers came from a 4-year-old plant growing in a commercial field at Windsor, Fla. and was taken in February of 2009.

Figure 2:
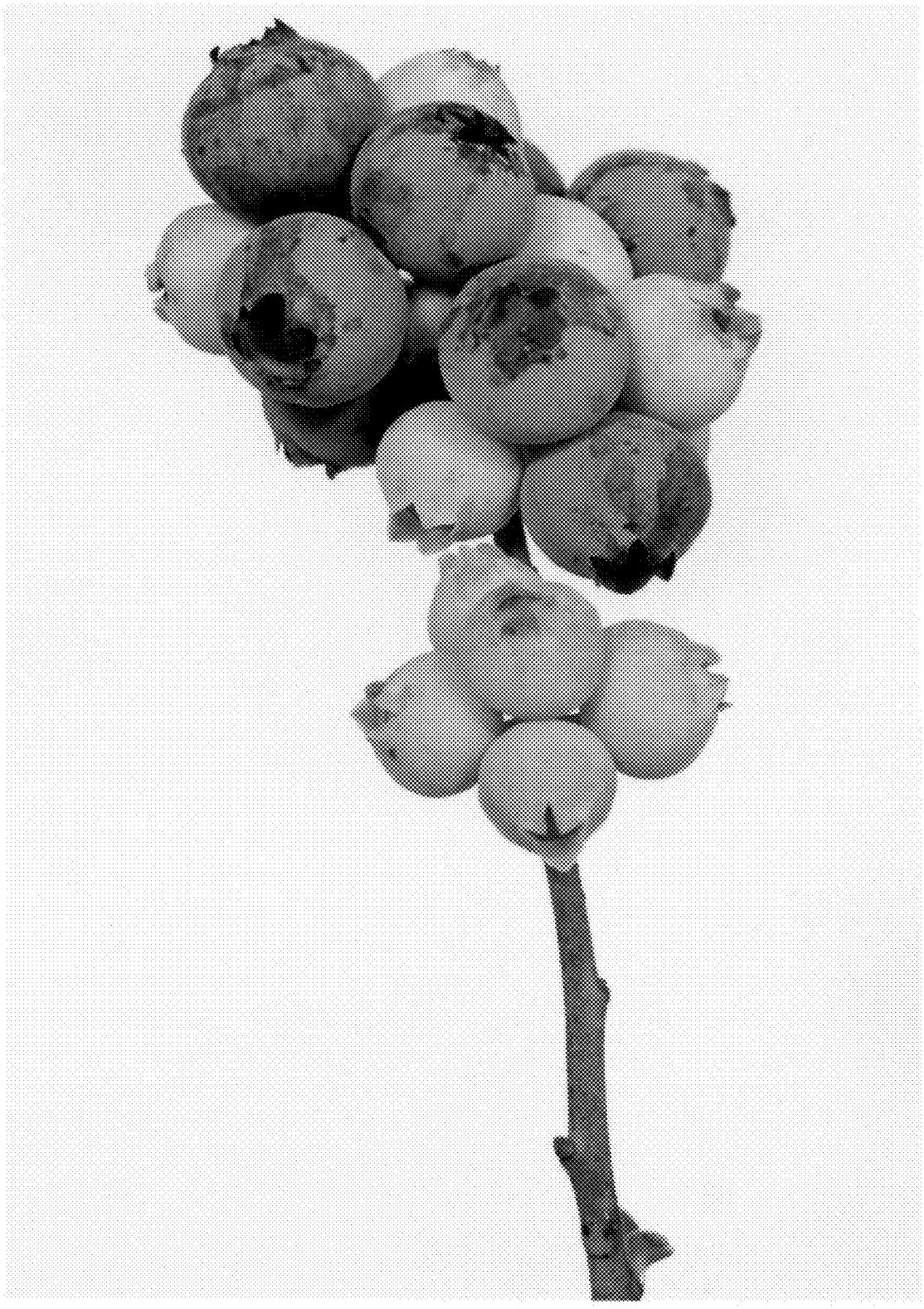
Figure 3:
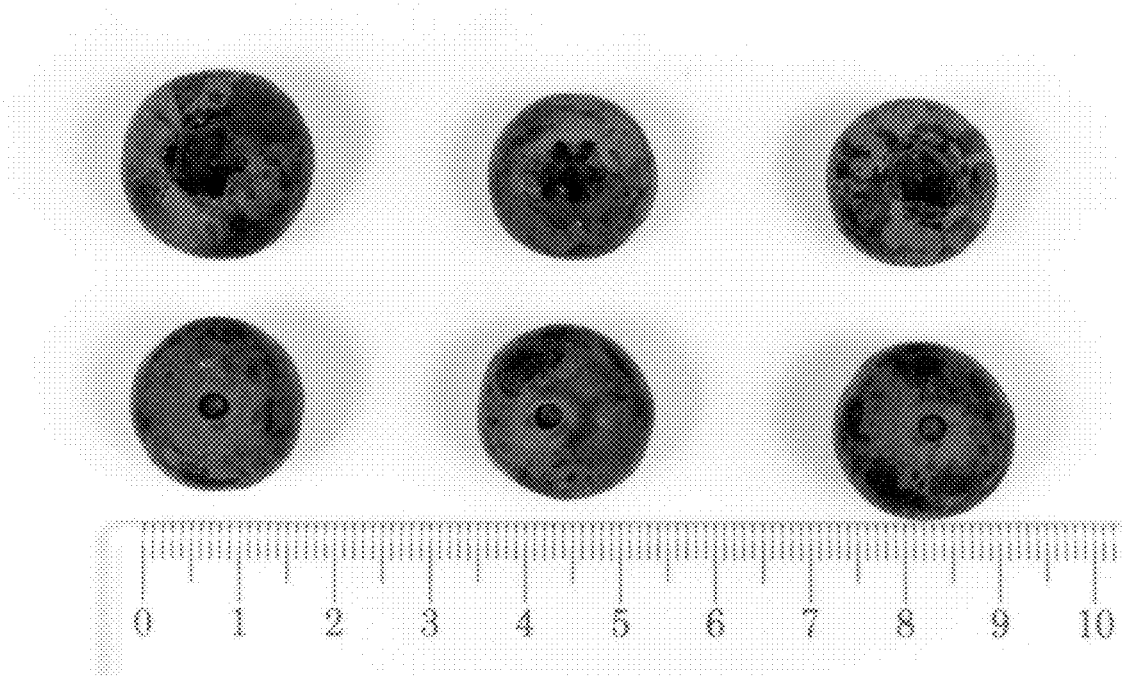

The photographs of the berries, FIG. 2 and FIG. 3, came from the same plant (as in FIG. 1) and were taken in April of 2009.

FIG. 1 shows a several clusters of opening flowers at full flowering in February, showing the urceolate flower shape and loose flower clusters.

FIG. 2 shows several clusters of berries ripening in the field. The freckling pattern is due to naturally occurring minerals in the water being used in overhead irrigation of the plants and is not an inherent feature of the berries. The berries are large and somewhat dark.

FIG. 3 shows berries at close range, showing the small dry picking scar and irregular calyx, which projects upward from the berry surface.

DESCRIPTION OF THE NEW CULTIVAR

The following detailed description sets forth the distinctive characteristics of 'FL04-235.' The detailed description was taken on 4-year-old plants growing under field conditions near Windsor in northeast Florida between February of 2009 and May of 2009, depending on the characteristics being described. The color chart used in this specification is "The Pantone Book of Color", by Leatrice Eiseman and Lawrence Herbert (1990). Harry N. Abrams, Inc., Publishers, N.Y. Where colors in the drawings differ from the Pantone color designations in the verbal descriptions, the Pantone color designations are accurate.

DETAILED BOTANICAL DESCRIPTION

Classification:

*Botanical name.*—*Vaccinium corymbosum* L.

*Common name.*—Southern highbush blueberry.

*Denomination.*—'FL04-235'.

Parentage:

*Female parent.*—'FL98-409' (unpatented).

*Male parent.*—'C97-390' (unpatented).

Market class: 'FL04-235' produces southern highbush blueberries suitable for both the fresh and processed fruit markets.

Bush description:

*Plant height.*—2.5 m.

*Canopy diameter* (*measured at the widest part of the bush*).—2.5 m.

*Vigor.*—High.

*Growth habit.*—Very upright.

*Twigginess.*—Low.

*Tendency toward evergreenness.*—Medium to high.

*Productivity.*—In northeast Florida, 'FL04-235' produces 4 to 6 pounds of berries per bush on plants 3 years old or older.

*Chilling requirement.*—100 hours below 7° C.

*Cold hardiness.*—Flowers and fruit are hardy to −3° C.; the plant, during winter dormancy, is hardy to −15° C.

*Ease of propagation.*—Easy to propagate from softwood cuttings; the plants survive and grow well in nursery beds.

Trunks and branches:

*Suckering tendency.*—Low; 4-year-old plants have an average of 4 major canes rising from a crown 30 cm in diameter.

*Surface texture* (*of strong, 6-month-old shoots observed in June*).—Smooth.

*Surface texture* (*of 3-year-old and older wood*).—Rough due to exfoliation and production of vertical cracks.

*Color of 4-month-old twigs observed in June in the field.*—"Lettuce Green", Pantone 13-0324.

*Color of 3-year-old rough-textured canes.*—"Parchment", Pantone 13-0908 Internode length on strong, upright shoots measured in June: Averages about 1.8 cm.

Leaves:

*Length, mean* (*including petiole, from tip of petiole to end of blade*).—5.6 cm.

*Width, mean* (*at widest point*).—2.4 cm.

*Shape.*—Ovate, terminating in a very short dew tip, 0.6 mm long, which is visible with a 15X microscope.

*Margin.*—Entire, but with approximately 5 sessile glands along each side.

*Apex.*—Acute.

*Base.*—Acute.

*Color.*—Upper surface: "Artichoke Green", Pantone 18-0125. Lower surface: "Piquant Green", Pantone 17-0235.

*Pubescence.*—Upper surface: Numerous white, short, curled hairs along the midrib and principle secondary veins. Lower surface: Numerous short, white, curled hairs along the midrib.

*Pubescence on margins.*—Absent.

*Relative time of leafing versus flowering.*—In commercial fields in north Florida, where the variety is sprayed with hydrogen cyanamide in midwinter, the variety begins to produce new leaves at the time of full bloom.

Flower:

*Arrangement.*—Flowers arranged alternately along a short, leafless, deciduous branch.

*Fragrance.*—Slight rose.

*Shape.*—Urceolate.

*Flowering period.*—Mean date of 50% open flowers in Windsor, Florida is January 28.

*Cluster habit.*—Loose.

*Median number of flowers per cluster.*—Median is 4.

*Petals.*—Fused into a corolla with 5 lobes.

*Pedicel.*—Length at time of anthesis: 1.0 cm. Color: "Almond Blossom", Pantone 13-2006.

*Peduncle.*—Length at time of anthesis: Highly variable; median is 1.2 cm. Color: "Almond Blossom", Pantone 13-2006.

*Calyx.*—Diameter of calyx aperture on mature berry (longest diameter): 0.7 cm. Surface texture: Smooth.

*Corolla.*—Length (from pedicel attachment to corolla tip excluding the pedicel): Median is 1.2 cm. Diameter of tube (at widest point): 1.0 cm. Aperture diameter: 0.4 cm to 0.5 cm. Surface texture: Smooth. Color at anthesis: White.

Reproductive organs:

*Style length* (*top of ovary to stigma tip*).—1.0 cm.

*Location of tip of stigma relative to lip of the corolla.*—Co-equal.

*Pollen.*—General: When the pollen is stained with 2% acetocarmine, the potential pollen fertility can be measured; 96% of the pollen tetrads appear normal and are stained. Abundance of shed: Very high. Color of dried pollen: "Winter White", Pantone 11-0507.

Self-fruitfulness: Medium to low; planting in field configurations that promote cross pollination with other southern highbush clones is recommended for all southern highbush in Florida.

Fruit:

*Mean date of first commercial harvest* (*25% of berries ripe*).—April 5.

*Mean date of mid-harvest.*—April 15.

*Mean date of last harvest.*—April 25.

*Size and shape of calyx lobes on mature berry.*—Irregularly shape; the calyx lobes project upward from the berry surface.

*Pedicel length on ripe berry.*—Median is 0.6 cm.

*Peduncle length on ripe berry.*—Variable; median is 1.0 cm.

*Detachment force for ripe berries.*—Medium to high.

*Number of berries per cluster.*—5.

Berry:

*Cluster habit.*—Loose.

*Weight* (*on well-pruned plants*).—2.4 g per berry.

*Height.*—1.5 cm.

*Width.*—1.7 cm.

*Shape.*—Subglobose; somewhat flattened top to bottom.

*Surface color of immature berries, with bloom.*—"Bone White", Pantone 12-0105.

*Surface color of mature berries while on the plant.*—"Pearl Blue", Pantone 14-4206.

*Surface color of ripe berry after polishing.*—Shiny black.

*Surface wax.*—Low to medium in amount and in persistence during handling of the berry.

*Pedicel scar.*—Small and dry.

*Firmness.*—Very high.

*Flavor.*—Sweet, low acidity.

*Texture.*—Good; small seeds, thin skin.

Seeds:

*Color of dried seeds.*—"Brown Sugar", Pantone 17-1134.

*Weight of well-developed dried seed.*—0.5 mg per seed.

*Length of well-developed dried seed.*—Mean is 0.2 cm.

Disease and insect resistance: 'FL04-235' has grown vigorously and shows good bush survival in the field. It appears to have above-average resistance to root rot (*Phytophthora cinnamomi*) and stem blight (*Botryosphaeria* spp.). The plants have shown no signs of cane canker (*Botryosphaeria corticis*) susceptibility in the field. The fungal leaf spots that are common on highbush blueberries grown in Florida are easily controlled by approved fungicides. The plants appear to have an above-average tendency to topple when carrying a very heavy ice load during freeze protection of the flowers with overhead irrigation. This is probably due to the upright growth and stiff canes.

COMPARISON WITH PARENTAL LINES AND KNOWN CULTIVARS

'FL04-235' is distinguished from the proprietary *Vaccinium corymbosum* L. female parent, 'FL98-409' (unpatented) in that 'FL04-235' has a higher berry firmess, a better picking scar and produces new leaves more prolifically after flowering than 'FL98-409'.

'FL04-235' is distinguished from the proprietary *Vaccinium corymbosum* L. male parent, 'C97-390' (unpatented) in that 'FL04-235' has a more upright plant habit, a firmer berry and a lower tendency towards evergreenness than 'C97-390'.

'FL04-235' is distinguished from the comparison commercial variety 'Primadonna' (U.S. Plant Pat. No. 20,181) in that 'FL04-235' has ovate-shaped leaves, while 'Primadonna' has elliptic-shaped leaves. Additionally, 'FL04-235' has larger berries (2.4 g per berry) than 'Primadonna' (2.13 g per berry).

'FL04-235' is distinguished from the comparison commercial variety 'Star' (U.S. Plant Pat. No. 10,675) in that 'FL04-235' has a more vigorous growth habit and upright plant habit and has a lower chilling requirement than 'Star'. Additionally, 'FL04-235' has a flowering period that is approximately 14 days earlier than 'Star' and berries that ripen approximately 12 days earlier than 'Star'.

I claim:

1. A new and distinct cultivar of southern highbush blueberry plant as shown and described herein.

* * * * *